(12) United States Patent
Bereznitski et al.

(10) Patent No.: US 7,875,642 B2
(45) Date of Patent: Jan. 25, 2011

(54) CRYSTALLINE FORMS OF AN INHIBITOR OF 11-β-HYDROXYSTEROID DEHYDROGENASE TYPE 1

(75) Inventors: Yuri Bereznitski, South River, NJ (US); Mark A. Huffman, Warren, NJ (US); Joseph E. Lynch, Plainfield, NJ (US); Matthew Zhao, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1217 days.

(21) Appl. No.: 10/587,110

(22) PCT Filed: Jan. 21, 2005

(86) PCT No.: PCT/US2005/001928

§ 371 (c)(1),
(2), (4) Date: Jul. 24, 2006

(87) PCT Pub. No.: WO2005/073200

PCT Pub. Date: Aug. 11, 2005

(65) Prior Publication Data

US 2009/0186928 A1    Jul. 23, 2009

Related U.S. Application Data

(60) Provisional application No. 60/539,206, filed on Jan. 26, 2004.

(51) Int. Cl.
*A61K 31/4196* (2006.01)
*C07D 249/08* (2006.01)

(52) U.S. Cl. .................................. 514/383; 548/262.2

(58) Field of Classification Search .................. 514/383; 548/262.2
See application file for complete search history.

(56) References Cited

U.S. PATENT DOCUMENTS

| | | | |
|---|---|---|---|
| 6,319,939 B1 | 11/2001 | Mabire et al. | |
| 6,503,935 B1 | 1/2003 | Altenbach et al. | |
| 6,730,690 B2 * | 5/2004 | Olson et al. | 514/383 |

(Continued)

FOREIGN PATENT DOCUMENTS

WO    WO 01/90094 A1    11/2001

(Continued)

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*

(Continued)

*Primary Examiner*—Rebecca L Anderson
*Assistant Examiner*—Matthew P Coughlin
(74) *Attorney, Agent, or Firm*—Heidi M. Struse; Richard C. Billups; John C. Todaro

(57) ABSTRACT

Novel crystalline salts of 3-[1-(4-chlorophenyl)-trans-3-fluorocyclobutyl]-4,5-dicyclopropyl-r-4H-1,2,4-triazole are potent inhibitors of 11β-hydroxysteroid dehydrogenase Type 1 and are useful for the treatment of conditions associated with Metabolic Syndrome as well as cognitive impairment. The invention also relates to pharmaceutical compositions containing these novel salts, processes to prepare these salts and their pharmaceutical compositions as well as uses thereof for the treatment of Type 2 diabetes, hyperglycemia, obesity, dyslipidemia, hypertension, and cognitive impairment.

20 Claims, 14 Drawing Sheets

U.S. PATENT DOCUMENTS

| | | |
|---|---|---|
| 7,179,802 B2 * | 2/2007 | Olson et al. ............. 514/211.1 |
| 2003/0073850 A1 | 4/2003 | Altenbach et al. |
| 2004/0048912 A1 * | 3/2004 | Olson et al. ................ 514/383 |
| 2004/0106664 A1 * | 6/2004 | Olson et al. ................ 514/383 |

FOREIGN PATENT DOCUMENTS

| | | |
|---|---|---|
| WO | WO 03/004497 A1 | 1/2003 |
| WO | 03104207 A2 | 12/2003 |
| WO | WO 03104207 A2 * | 12/2003 |
| WO | WO 03104208 A1 * | 12/2003 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

Reimlinger, H. et al., "Synthesen von s-Triazolo[3.4-a]isochinolinen" Chem. Ber,vol. 103, pp. 1960-1970, 1970.

* cited by examiner

CRYSTALLINE FORMS OF AN INHIBITOR OF 11-β-HYDROXYSTEROID DEHYDROGENASE TYPE 1

CROSS REFERENCE TO RELATED APPLICATIONS

This application is a US National phase Application No. PCT/US2005/001928, filed Jan. 21, 2005, which was based upon U.S. provisional application No. 60/539,206 filed on Jan. 26, 2004, priority of which is claimed hereunder.

FIELD OF THE INVENTION

The present invention relates to novel crystalline forms of an inhibitor of 11β-hydroxysteroid dehydrogenase Type 1. More particularly, the invention relates to a novel crystalline anhydrate and a novel crystalline monohydrate of 3-[1-(4-chlorophenyl)-trans-3-fluorocyclobutyl]-4,5-dicyclopropyl-r-4H-1,2,4-triazole, which is a potent inhibitor of the 11β-hydroxysteroid dehydrogenase Type 1(11β-HSD-1) enzyme. These novel crystalline forms of the 11β-HSD-1 inhibitor are useful for the preparation of pharmaceutical compositions containing the inhibitor for the treatment and prevention of diseases and conditions for which an inhibitor of 11β-HSD-1 is indicated, in particular Type 2 diabetes, hyperglycemia, obesity, dyslipidemia, hypertension, and cognitive impairment. The invention further concerns pharmaceutical compositions comprising the novel crystalline polymorphic forms of the present invention; processes for preparing the particular anhydrate and monohydrate forms and their pharmaceutical compositions; and methods of treating conditions for which an inhibitor of 11β-HSD-1 is indicated comprising administering a composition of the present invention.

BACKGROUND OF THE INVENTION

Inhibition of 11β-hydroxysteroid dehydrogenase Type 1(11β-HSD-1), an enzyme that catalyzes regeneration of active 11-hydroxy glucocorticoids from inactive 11-keto metabolites within target tissues, represents a novel approach to the treatment of the conditions associated with the Metabolic Syndrome, including hypertension, obesity, dyslipidemia, and Type 2 diabetes, also known as non-insulin dependent diabetes mellitus (NIDDM). Inhibitors of this enzyme may also have utility to treat or prevent age-associated cognitive impairment. The therapeutic potential of inhibitors of 11β-HSD-1 has been reviewed: B. R. Walker and J. R. Seckl, "11β-Hydroxysteroid dehydrogenase Type 1 as a novel therapeutic target in metabolic and neurodegenerative disease," *Expert Opin. Ther. Targets*, 7: 771-783 (2003).

WO 03/104207 (published 18 Dec. 2003), assigned to Merck & Co., describes a class of substituted 1,2,4-triazoles, which are potent inhibitors of the 11β-HSD-1 enzyme and therefore useful for the treatment of Type 2 diabetes, hyperglycemia, obesity, dyslipidemia, hypertension, and cognitive impairment. Specifically disclosed in WO 03/104207 is 3-[1-(4-chlorophenyl)-trans-3-fluorocyclobutyl]-4,5-dicyclopropyl-r-4H-1,2,4-triazole.

However, there is no disclosure in WO 03/104207 of the newly discovered crystalline monohydrate and anhydrate forms of 3-[1-(4-chlorophenyl)-trans-3-fluorocyclobutyl]-4,5-dicyclopropyl-r-4H-1,2,4-triazole of structural formula I below (hereinafter referred to as Compound I).

The present invention also discloses a novel crystalline toluene solvate of Compound I.

SUMMARY OF THE INVENTION

The present invention is concerned with a novel crystalline monohydrate and crystalline anhydrate of the 11β-hydroxysteroid dehydrogenase Type 1 (11β-HSD-1) inhibitor 3-[1-(4-chlorophenyl)-trans-3-fluorocyclobutyl]-4,5-dicyclopropyl-r-4H-1,2,4-triazole of structural formula I (Compound I). The crystalline monohydrate and the crystalline anhydrate forms of the present invention have advantages over the previously disclosed amorphous form of 3-[1-(4-chlorophenyl)-trans-3-fluorocyclobutyl]-4,5-dicyclopropyl-r-4H-1,2,4-triazole in the preparation of pharmaceutical compositions, such as ease of processing, handling, and dosing. In particular, they exhibit improved physicochemical properties, such as stability to stress, rendering them particularly suitable for the manufacture of various pharmaceutical dosage forms. The invention also concerns pharmaceutical compositions containing the novel crystalline polymorphs; processes for the preparation of these polymorphic forms and their pharmaceutical compositions; and methods for using them for the prevention or treatment of Type 2 diabetes, hyperglycemia, obesity, dyslipidemia, hypertension, and cognitive impairment.

DETAILED DESCRIPTION OF THE INVENTION

Figure 1:
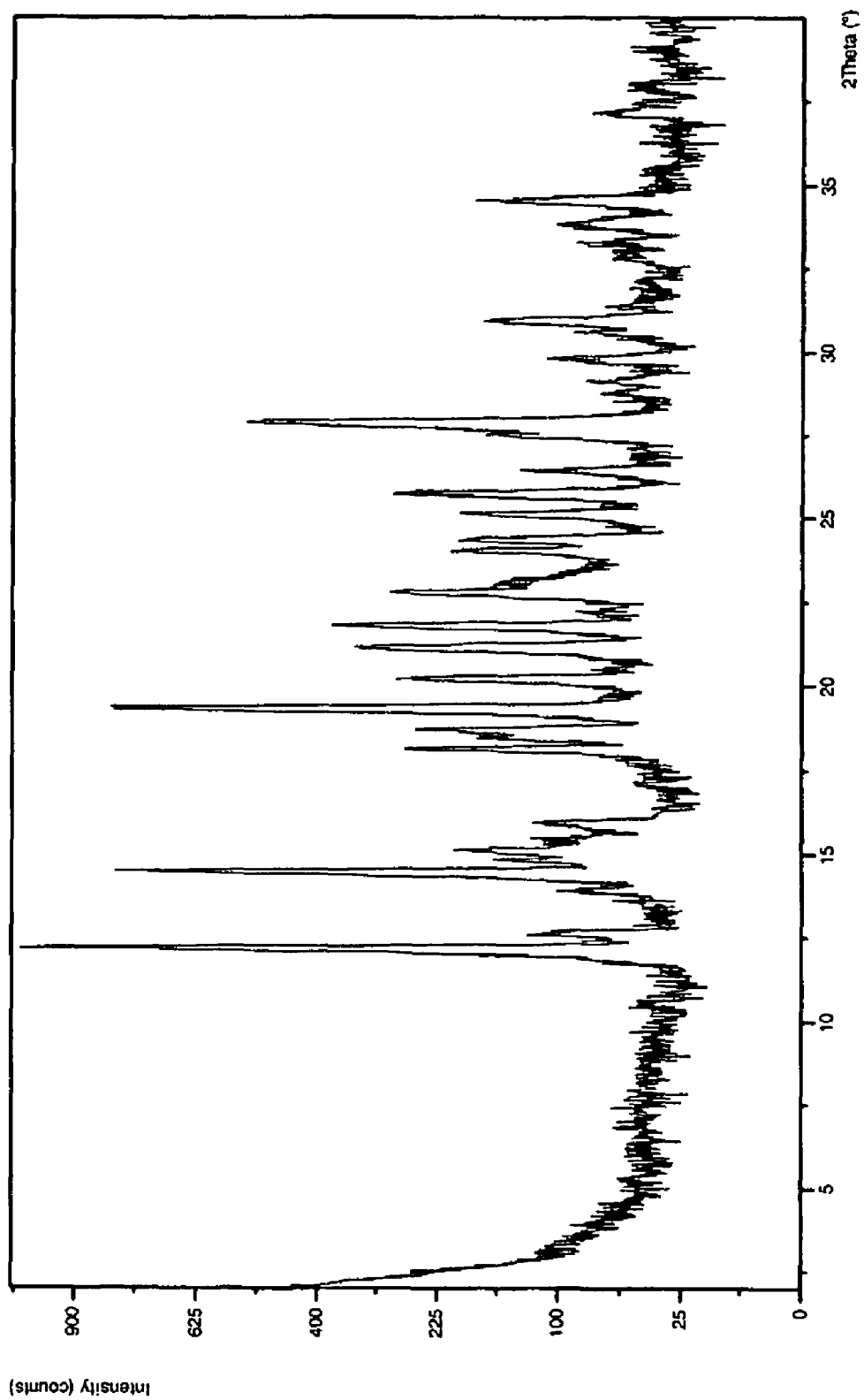
FIG. 1 is a characteristic X-ray diffraction pattern of the crystalline anhydrate form of Compound I of the present invention.

This invention provides novel crystalline monohydrate and anhydrate polymorphic forms of 3-[1-(4-chlorophenyl)-trans-3-fluorocyclobutyl]-4,5-dicyclopropyl-r-4H-1,2,4-triazole of structural formula I (Compound I):

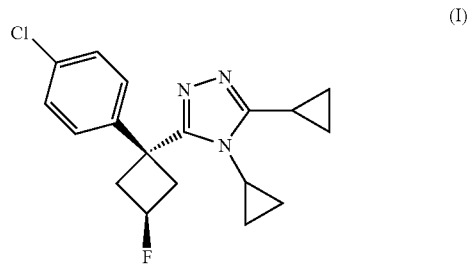

(I)

A further embodiment of the present invention provides the Compound I drug substance that comprises the crystalline anhydrate or crystalline monohydrate form in a detectable amount. By "drug substance" is meant the active pharmaceutical ingredient (API). The amount of crystalline anhydrate form or crystalline monohydrate form in the drug substance can be quantified by the use of physical methods such as X-ray powder diffraction (XRPD), solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy. In a class of this embodiment, about 5% to about 100% by weight of the crystalline anhydrate or crystalline monohydrate form is present in the drug substance. In a second class of this embodiment, about 10% to about 100% by weight of the crystalline anhydrate or crystalline monohydrate form is present in the drug substance. In a third class of this embodiment, about 25% to about 100% by weight of the crystalline anhydrate or crystalline monohydrate form is present in the drug substance. In a fourth class of this embodiment, about 50% to about 100% by weight of the crystalline anhydrate or crystalline monohydrate form is present in the drug substance. In a fifth class of this embodiment, about 75% to about 100% by weight of the crystalline anhydrate or crystalline monohydrate form is present in the drug substance. In a sixth class of this embodiment, substantially all of the Compound I drug substance is the crystalline anhydrate or crystalline monohydrate form, i.e., the Compound I drug substance is substantially phase pure crystalline anhydrate or crystalline monohydrate form.

Another aspect of the present invention provides a novel crystalline toluene solvate of Compound I which has utility as an intermediate in the preparation of the crystalline anhydrate and crystalline monohydrate forms of the present invention.

Another aspect of the present invention provides a method for the prevention or treatment of clinical conditions for which an inhibitor of 11β-HSD-1 is indicated, which method comprises administering to a patient in need of such prevention or treatment a prophylactically or therapeutically effective amount of the crystalline anhydrate or crystalline monohydrate of Compound I or a pharmaceutical composition containing a prophylactically or therapeutically effective amount of the crystalline anhydrate or crystalline monohydrate form of Compound I. Such clinical conditions include Type 2 diabetes, hyperglycemia, obesity, dyslipidemia, hypertension, and cognitive impairment.

The present invention also provides for the use of the crystalline anhydrate or crystalline monohydrate form of the present invention in the manufacture of a medicament for the prevention or treatment in a mammal of clinical conditions for which an inhibitor of 11β-HSD-1 is indicated. In one embodiment the clinical condition is Type 2 diabetes.

Another aspect of the present invention provides the crystalline anhydrate or crystalline monohydrate form for use in the prevention or treatment in a mammal of clinical conditions for which an inhibitor of 11β-HSD-1 is indicated. In one embodiment of this aspect the clinical condition is Type 2 diabetes.

The present invention also provides pharmaceutical compositions comprising the crystalline anhydrate or crystalline monohydrate form, in association with one or more pharmaceutically acceptable carriers or excipients. In one embodiment the pharmaceutical composition comprises a prophylactically or therapeutically effective amount of the active pharmaceutical ingredient (API) in admixture with pharmaceutically acceptable excipients wherein the API comprises a detectable amount of the crystalline anhydrate form or crystalline monohydrate form of the present invention. In a second embodiment the pharmaceutical composition comprises a prophylactically or therapeutically effective amount of the API in admixture with pharmaceutically acceptable excipients wherein the API comprises about 5% to about 100% by weight of the crystalline anhydrate or crystalline monohydrate form of the present invention. In a class of this second embodiment, the API in such compositions comprises about 10% to about 100% by weight of the crystalline anhydrate or crystalline monohydrate form. In a second class of this embodiment, the API in such compositions comprises about 25% to about 100% by weight of the crystalline anhydrate or crystalline monohydrate form. In a third class of this embodiment, the API in such compositions comprises about 50% to about 100% by weight of the crystalline anhydrate or crystalline monohydrate form. In a fourth class of this embodiment, the API in such compositions comprises about 75% to about 100% by weight of the crystalline anhydrate or crystalline monohydrate form. In a fifth class of this embodiment, substantially all of the API is the crystalline anhydrate or crystalline monohydrate form of Compound I, i.e., the API is substantially phase pure Compound I crystalline anhydrate form or Compound I crystalline monohydrate form.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17th ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200, and 500 milligrams of the API for the symptomatic adjustment of the dosage to the patient to be treated. A medicament typically contains from about 0.5 mg to about 500 mg of the API, preferably, from about 1 mg to about 200 mg of API. Intravenously, the most preferred doses will range from about 0.1 to about 10 mg/kg/minute during a constant rate infusion. Advantageously, the crystalline anhydrate and monohydrate forms of the present invention may be administered in a single daily dose, or the total daily dosage may be administered in divided doses of two, three or four times daily. Furthermore, the crystalline anhydrate and monohydrate forms of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the Compound I crystalline anhydrate form and crystalline monohydrate form herein described in detail can form the API, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral API can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The following non-limiting Examples are intended to illustrate the present invention and should not be construed as being limitations on the scope or spirit of the instant invention.

Compound I described herein may exist as tautomers such as keto-enol tautomers. The individual tautomers as well as mixtures thereof are encompassed within the compound of structural formula I.

General Conditions For Preferentially Crystallizing Monohydrate Form

The monohydrate form can be crystallized from water or from mixtures of water with organic solvents such as methanol, ethanol, propanol, isopropanol, acetonitrile, tetrahydrofuran, N,N-dimethylformamide, N,N-dimethylacetamide, and N-methylpyrrolidinone. Crystallization can be induced by cooling, evaporation of solvent, or addition of water. The anhydrate form can be converted into the monohydrate form by suspending the anhydrate in water or mixtures of water with organic solvents, or by long-term exposure of the anhydrate to a high-humidity atmosphere.

General Conditions For Preferentially Crystallizing Anhydrate Form

The anhydrate form can be crystallized from numerous organic solvents and solvent mixtures. These include methyl acetate, ethyl acetate, isopropyl acetate, n-butyl acetate, isobutyl acetate, toluene, acetone, 2-butanone, tetrahydrofuran, methyl t-butyl ether, and mixtures with pentane, hexanes, heptane, octane, and isooctane. Crystallization can be induced by cooling, evaporation, or addition of a non-polar solvent, such as hexanes or heptane. The monohydrate form can be converted into the anhydrate form using a drying process in a low humidity atmosphere.

General Conditions for Preparing the Crystalline Toluene Solvate

The crystalline toluene solvate can be prepared by stirring a mixture of the anhydrate in toluene for 3 days. The toluene solvate was characterized by physical methods as described below. The toluene solvate can be re-converted into the crystalline anhydrate by drying the toluene solvate under vacuum at 40° C. for 3 days.

Preparation of 1-(4-chlorophenyl)-trans-3-fluorocyclobutane-r-carbohydrazide bisulfate salt (2-11)

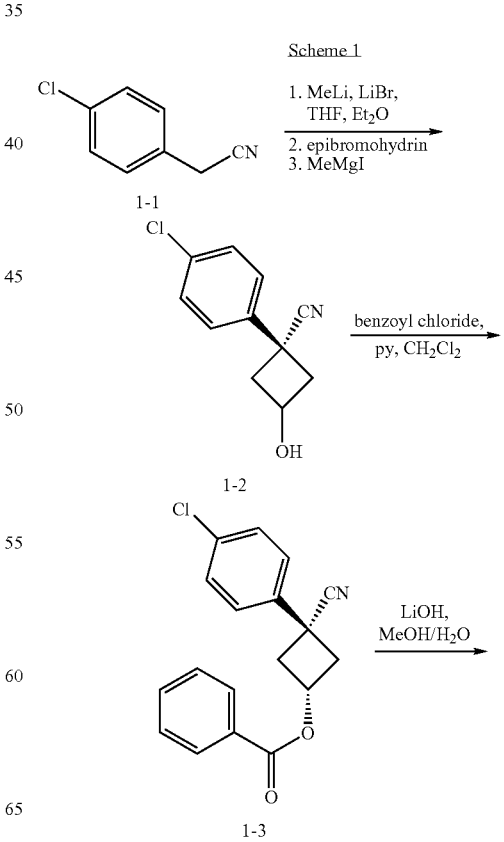

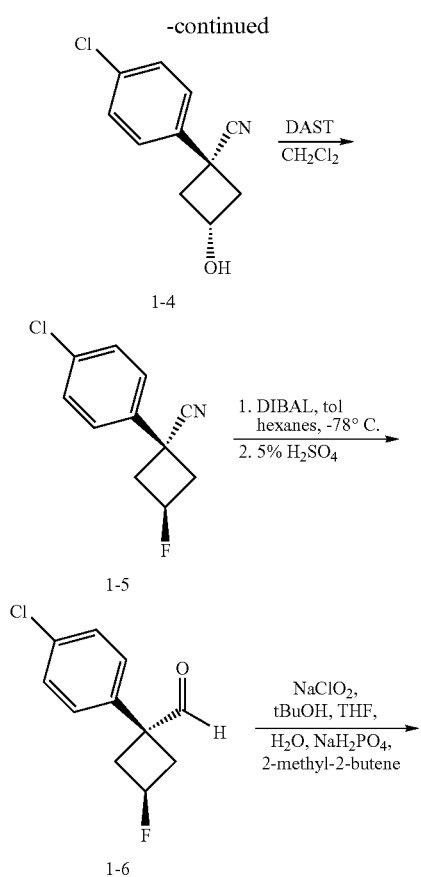

Step A (4-Chlorophenyl)acetonitrile (1-1) (14.04 g) was dissolved in freshly distilled tetrahydrofuran (250 mL) and stirred at −78° C. under argon. Methyl lithium (LiBr complex, 1.5 M in diethyl ether, 62 mL, 1 eq) was added dropwise such that the reaction temperature stayed below −66° C. The solution was stirred for one h at −78° C. and turned from yellow to deep red. Epibromohydrin was added dropwise and the solution was stirred for an additional 90 min. Methylmagnesium iodide (3.0 M in diethyl ether, 31 mL) was added and the solution turned light brown as it was slowly warmed to room temperature and stirred overnight. The reaction was quenched with water (75 mL) and acidified to pH 2 with 5 N aqueous hydrochloric acid (ca. 30 mL). Brine was added until the layers separated. The organic layer was collected and the aqueous layer was reextracted with diethyl ether (2×50 mL). The organic layers were combined, dried with magnesium sulfate, filtered and concentrated to give crude 1-(4-chlorophenyl)-3-hydroxycyclobutane-1-carbonitrile (1-2).

Step B

The crude 1-(4-chlorophenyl)-3-hydroxycyclobutane-1-carbonitrile (1-2) (ca. 4.2:1 ratio of cis:trans isomers) was dissolved in dichloromethane (150 mL) and stirred at 0° C. Pyridine (11.3 mL) and then benzoyl chloride (10.8 mL) were added and the solution was warmed to room temperature and stirred for 2.5 h. Additional pyridine (2 mL) and benzoyl chloride (2 mL) were added and the reaction was stirred at 30° C. overnight. The reaction was added to a saturated sodium bicarbonate solution and extracted with dichloromethane. The organic layer was washed with saturated ammonium chloride, dried over magnesium chloride, filtered and concentrated to give a reddish oil. The two isomers were separated by silica gel chromatography (25% dichloromethane/hexanes→33% dichloromethane/hexanes→50% dichloromethane/hexanes→100% dichloromethane) to give the desired 3-(4-chlorophenyl)-cis-3-cyanocyclobutyl benzoate (1-3).

Step C 3-(4-Chlorophenyl)-cis-3-cyanocyclobutyl benzoate (1-3) (6.42 g) was dissolved in methanol/tetrahydrofuran (10 mL/20 mL) and stirred at room temperature. Lithium hydroxide monohydrate (1.1 g) was dissolved in water (10 mL) and added to the benzoate solution. After 10 minutes, solid ammonium chloride (ca. 2 g) was added and the volatile solvents were removed by evaporation. The remaining aqueous mixture was extracted with diethyl ether, and the organic layer was dried with magnesium sulfate, filtered, and concentrated to give the desired cyclobutanol 1-4.

Step D

A portion of the 1-(4-chlorophenyl)-cis-3-hydroxycyclobutane-r-carbonitrile (1-4) (1.13 g) was dissolved in anhydrous dichloromethane and stirred at 0° C. (Diethylamino)sulfur trifluoride (DAST, 1.43 g) was added and the solution was warmed to 40° C. for 10 h. Additional DAST (0.5 mL) was added and the reaction was stirred overnight at 40° C. The solution was cooled, added to saturated aqueous sodium bicarbonate, and extracted twice with dichloromethane. The organic extracts were combined, dried with magnesium sulfate, filtered and concentrated. The crude residue was carefully chromatographed on silica gel (10% ethyl acetate/hexanes→20% ethyl acetate/hexanes→25% ethyl acetate/hexanes) to give 1-(4-chlorophenyl)-trans-3-fluorocyclobutane-r-carbonitrile (1-5).

Step E 1-(4-Chlorophenyl)-trans-3-fluorocyclobutane-r-carbonitrile (1-5) (1.65 g) was dissolved in anhydrous toluene (30 mL) and cooled to −78° C. A solution of diisobutylaluminum hydride (DIBAL, 1 M in hexanes, 9.4 mL) was added over 10 min, and the solution was stirred for 30 min. The reaction was quenched by adding 5% sulfuric acid (2.5 mL) and warmed to room temperature. After one hour, the mixture was filtered through a pad of celite. The pad was washed with ethyl acetate, and the entire filtrate was poured into water (20 mL). After separating the layers, the aqueous solution was extracted with ethyl acetate. The organic layers were combined, dried with magnesium sulfate, filtered and concentrated to give aldehyde 1-6.

Step F

The crude aldehyde 1-6 was dissolved in t-butanol/tetrahydrofuran/2-methylbut-2-ene (15 mL/5 mL/5 mL) and stirred at room temperature. Sodium chlorite (1.56 g) and sodium dihydrogenphosphate (2.39 g) were dissolved in water (7 mL), and added to the vigorously stirring solution. After 80 minutes, the volatile solvents were removed under vacuum and the mixture was acidified to pH 2 with aqueous 1N hydrochloric acid. The product was extracted with ethyl acetate (3×30 mL). The extracts were combined, dried over magnesium sulfate, filtered, and evaporated to give the desired carboxylic acid 1-7.

Step G 1-(4-Chlorophenyl)-trans-3-fluorocyclobutane-r-carboxylic acid (1-7) (5.68 g) was dissolved in dichloromethane/methanol (40 mL/10 mL). (Trimethylsilyl)diazomethane (15 mL, 2.0 M in hexanes) was added until the yellow color remained. After stirring at room temperature for one hour, acetic acid (2 mL) was added to quench the (trimethylsilyl)diazomethane, and the solution was concentrated to give methyl 1-(4-chlorophenyl)-trans-3-fluorocyclobutane-r-carboxylate. The crude methyl ester (5.8 g) was dissolved in toluene (15 mL). Anhydrous hydrazine (3.1 mL, 98.8 mmol) was added and the reaction was refluxed for two days. After cooling to room temperature and removing the toluene under vacuum, the product was purified by silica gel chromatography (100% ethyl acetate) to give 1-(4-chlorophenyl)-trans-3-fluorocyclobutane-r-carbohydrazide (1-8) as a white solid.

Scheme 2

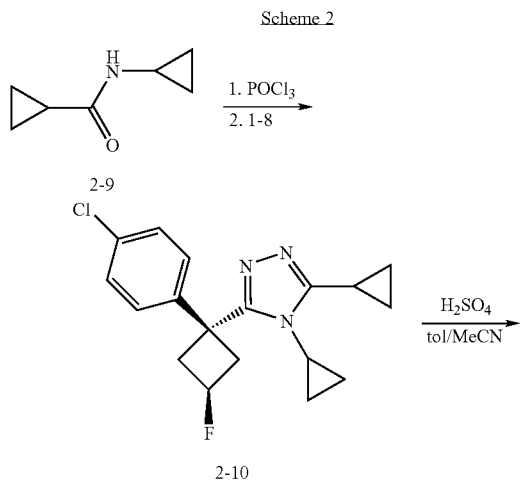

2-9

2-10

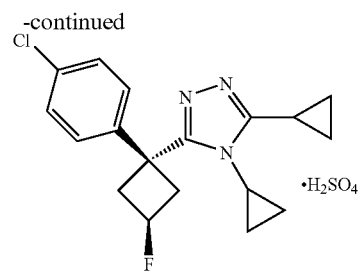

2-11

To a slurry of N-cyclopropylcyclopropanecarboxamide (2-9) [prepared as described in H. Hart and O. E. Curtis, Jr., *J. Amer. Chem. Soc.*, 78: 112-116 (1956)] (2.7 kg, 21.6 mol) in toluene (18 L) was added $POCl_3$ (6.63 kg, 43.2 mol). The mixture was heated to 35° C. and aged for 3 h. It was then cooled to 0-5° C. and the hydrazide 1-8 (4.37 kg, 18.0 mol) was added in portions maintaining the batch below 10° C. The mixture was then slowly warmed to 21° C. overnight. The reaction mixture was then cooled to 0-5° C. and slowly quenched into vigorously stirred aqueous NaOH (6.0 N, 39.0 L) at below 5° C. rinsing forward with toluene (2 L). The mixture was stirred for 1 h, then NaOH (6 N, 0.6 L) and acetonitrile (10 L) were added. Triethylamine (546 g, 0.75 L) was added and the mixture was heated to 55° C. overnight. It was then cooled to 35° C. and acetic acid (4.3 L, 72 mol) was added. The mixture was stirred at 35° C. for 3 h to effect cyclization, then cooled to 21° C. The aqueous layer was discarded and the organic layer was washed twice with water (36 L). The organic layer was concentrated to about 20 L and then acetonitrile (21 L) was added. Concentrated sulfuric acid (1.76 kg, 0.96 L) was added slowly to form the bisulfate salt 2-11. The product was filtered and washed with 1:1 acetonitrile/toluene (18 L), then dried under vacuum at 40° C. to give the bisulfate salt.

Example 1

3-[1-(4-chlorophenyl)-trans-3-fluorocyclobutyl]-4,5-dicyclopropyl-r-4H-1,2,4-triazole crystalline anhydrate A slurry of the bisulfate salt 2-11 (39.0 g, 90.9 mmol) in IPAc (150 mL) was mixed with 10% $Na_2CO_3$ (100 mL) until all solid dissolved. The aqueous layer was removed and the organic layer was washed twice with 50 mL of water. The organic layer was then concentrated in vacuo to 70 g (about 45 mL residual IPAc). Some product crystallized during concentration. Heptane (180 mL) was added slowly and the mixture was aged for 2 h. The product was filtered and the filter cake washed with heptane. Air drying followed by oven drying at 40° C. gave the crystalline anhydrate free base as a white solid.

Example 2

3-[1-(4-chlorophenyl)-trans-3-fluorocyclobutyl]-4,5-dicyclopropyl-r-4H-1,2,4-triazole crystalline anhydrate To a slurry of the bisulfate salt 2-11 (9.75 g, 22.7 mmol) in toluene (60 mL) was added water (60 mL) and 50% NaOH (4.54 g, 56.8 mmol). The mixture was stirred until all the solid dissolved. The aqueous layer was discarded. The organic layer was washed with aqueous 5% NaCl (60 mL). The organic layer was concentrated by vacuum distillation to about 38 mL. The solution was then transferred through an inline filter into a stirring suspension of the free base seed crystals (483 mg) in heptane (135 mL) over 3 h. The resulting mixture was cooled to 0° C. and stirred for 30 min, then filtered rinsing with 4:1 heptane-toluene (30 mL) followed by heptane (30 mL). The crystalline material was dried under vacuum at 40° C. to give the crystalline anhydrate form.

Example 3

3-[1-(4-chlorophenyl)-trans-3-fluorocyclobutyl]-4,5-dicyclopropyl-r-4H-1,2,4-triazole crystalline monohydrate To a slurry of 6.58 g bisulfate salt 2-11 in IPA (15 mL) were added water (7.5 mL) and 10 N NaOH (3.2 mL). The mixture was warmed to 40° C. until all solid dissolved. The aqueous layer was separated and then more water (7.5 mL) was added to the organic layer. The mixture was seeded with anhydrous free base and aged for 0.5 h. More water (30 mL) was added slowly over 3 h via a syringe pump. The mixture was aged overnight and filtered. The filter cake was rinsed with 3:1 water/IPA (20 mL) and then water (40 mL). Air drying overnight gave the crystalline monohydrate form.

3-[1-(4-chlorophenyl)-trans-3-fluorocyclobutyl]-4,5-dicyclopropyl-r-4H-1,2,4-triazole crystalline anhydrate The monohydrate was then dehydrated by drying in a vacuum oven at 40° C. with a slow nitrogen sweep to give the crystalline anhydrate form.

X-ray powder diffraction studies are widely used to characterize molecular structures, crystallinity, and polymorphism. The X-ray powder diffraction patterns of the crystalline polymorphs of the present invention were generated on a Philips Analytical X'Pert PRO X-ray Diffraction System with PW3040/60 console. A PW3373/00 ceramic Cu LEF X-ray tube K-Alpha radiation was used as the source.

FIG. 1 shows an X-ray diffraction pattern for the crystalline anhydrate form. The anhydrate form exhibited characteristic reflections corresponding to d-spacings of 7.19, 6.09, 4.57, 4.19, 4.06, and 3.20 angstroms.

Figure 6:
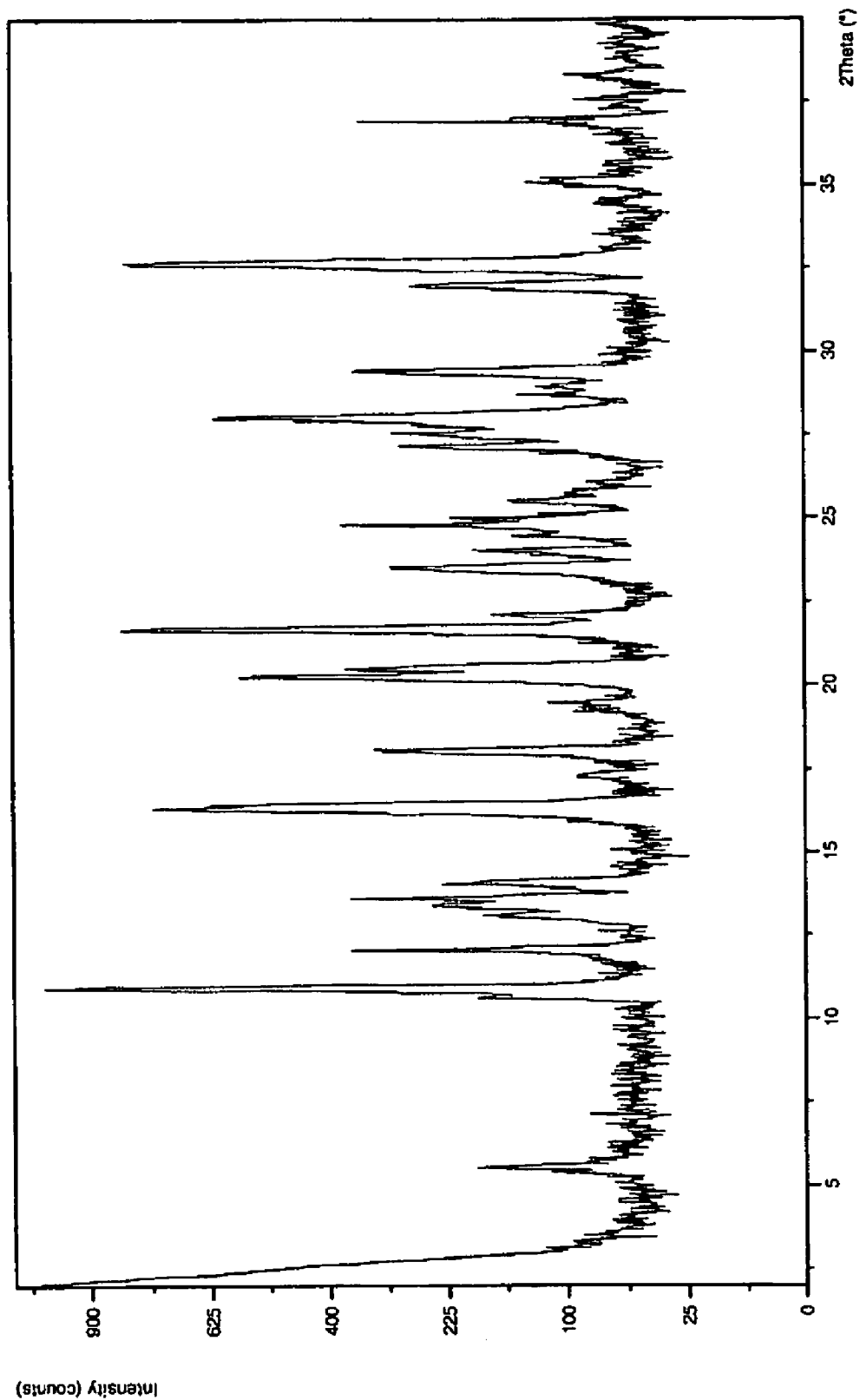
FIG. 6 is a characteristic X-ray diffraction pattern of the crystalline monohydrate form of Compound I of the present invention.

FIG. 6 shows an X-ray diffraction pattern for the crystalline monohydrate form. The monohydrate form exhibited characteristic reflections corresponding to d-spacings of 8.08, 6.49, 5.43, 5.39, 4.38, 4.10, 3.18, and 2.74 angstroms.

Figure 11:
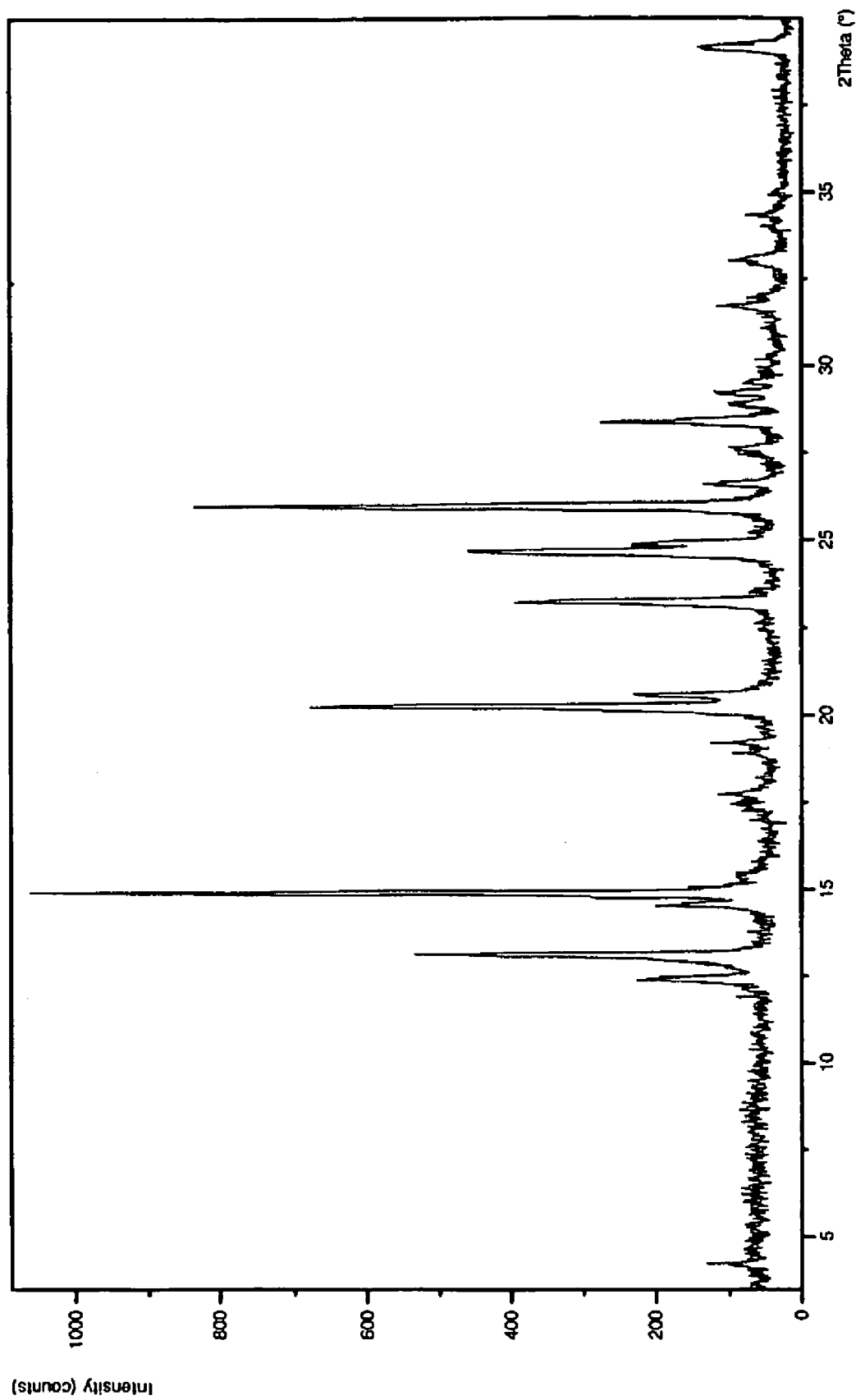
FIG. 11 is a characteristic X-ray diffraction pattern of the crystalline toluene solvate of Compound I of the present invention.

FIG. 11 shows an X-ray diffraction pattern for the crystalline toluene solvate. The toluene solvate exhibited characteristic reflections corresponding to d-spacings of 7.13, 6.74, 5.95, 4.38, 3.83, 3.61, 3.42, 3.14, and 2.30 angstroms.

In addition to the X-ray powder diffraction patterns described above, the crystalline polymorphic forms of Compound I of the present invention were further characterized by their solid-state carbon-13 and fluorine-19 nuclear magnetic resonance (NMR) spectra. The solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 1024 scans were collected with a recycle delay of 5 seconds. A line broadening of 40 Hz was applied to the spectrum before FT was performed. Chemical shifts are reported on the TMS scale using the carbonyl carbon of glycine (176.03 p.p.m.) as a secondary reference.

The solid-state fluorine-19 NMR spectrum was obtained on a Bruker DSX 400WB NMR system using a Bruker 4 mm CRAMPS probe. The NMR spectrum utilized a simple pulse-acquire pulse program. The samples were spun at 15.0 kHz, and a total of 128 scans were collected with a recycle delay of 5 seconds. A vespel endcap was utilized to minimize fluorine background. A line broadening of 100 Hz was applied to the spectrum before FT was performed. Chemical shifts are reported using poly(tetrafluoroethylene) (teflon) as an external secondary reference which was assigned a chemical shift of −122 ppm.

Figure 2:
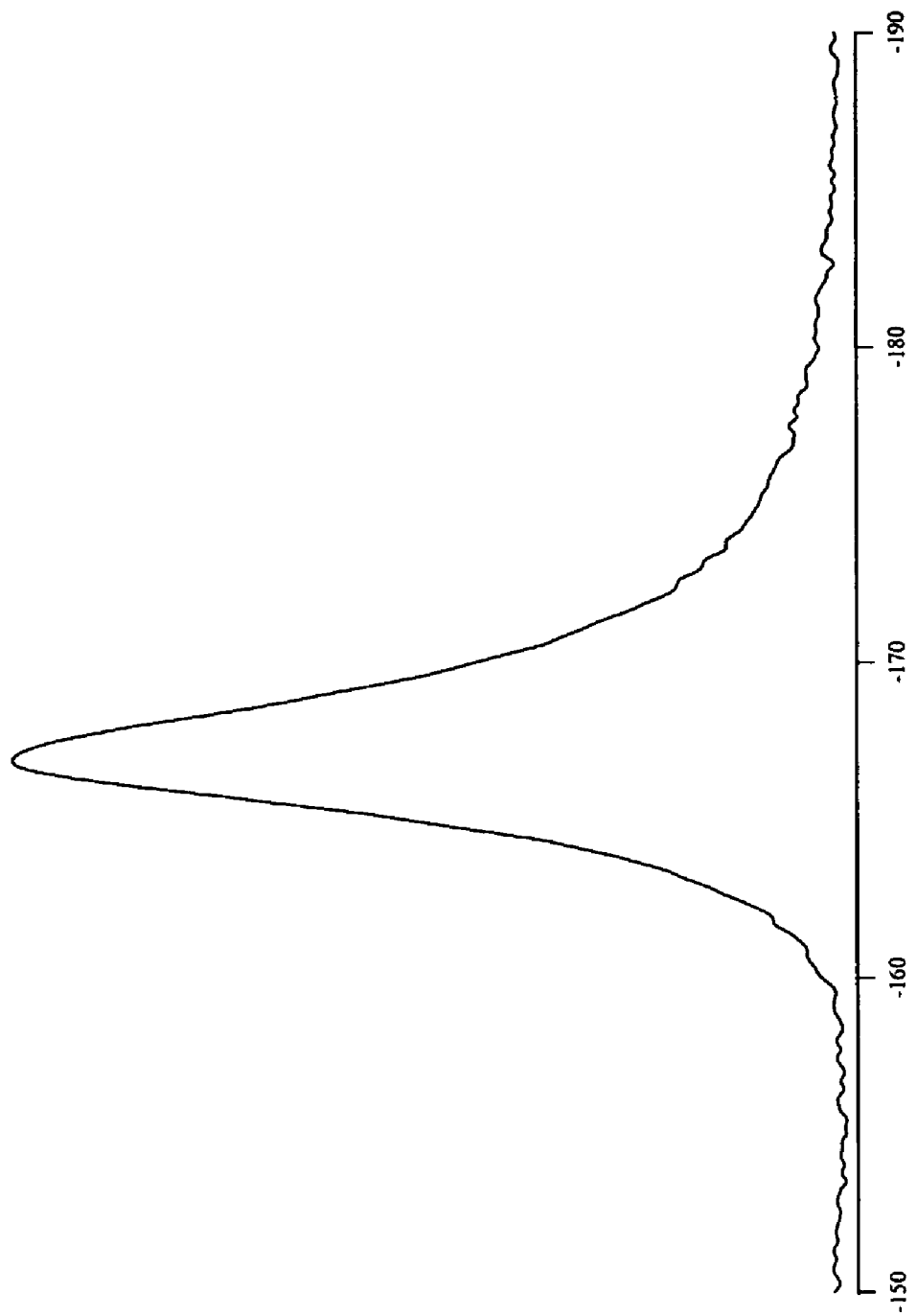
FIG. 2 is a fluorine-19 magic-angle spinning (MAS) nuclear magnetic resonance (NMR) spectrum of the crystalline anhydrate form of Compound I of the present invention.

FIG. 2 shows the solid-state fluorine-19 MAS NMR spectrum for the crystalline anhydrate form of Compound I. The crystalline anhydrate exhibited an isotropic peak at −167 p.p.m.

Figure 3:
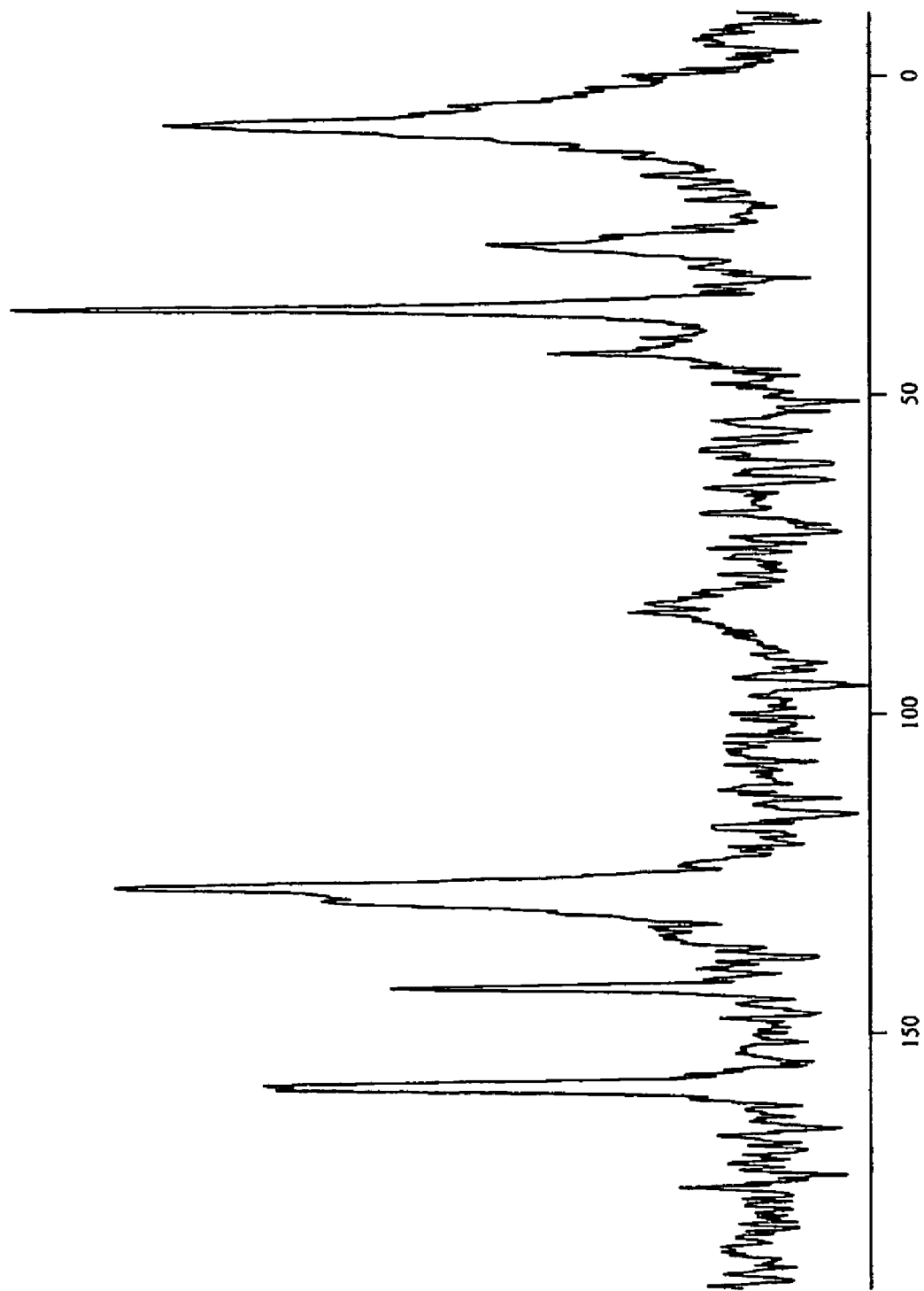
FIG. 3 is a carbon-13 cross-polarization magic-angle spinning (CPMAS) nuclear magnetic resonance (NMR) spectrum of the crystalline anhydrate form of Compound I of the present invention.

FIG. 3 shows the solid state carbon-13 CPMAS NMR spectrum for the crystalline anhydrate form of Compound I. The crystalline anhydrate form exhibited characteristic signals with chemical shift values of 158.9, 158.2, 143.0, 129.3, 127.2, 43.5, 36.6, 26.4, and 7.6 p.p.m.

Figure 7:
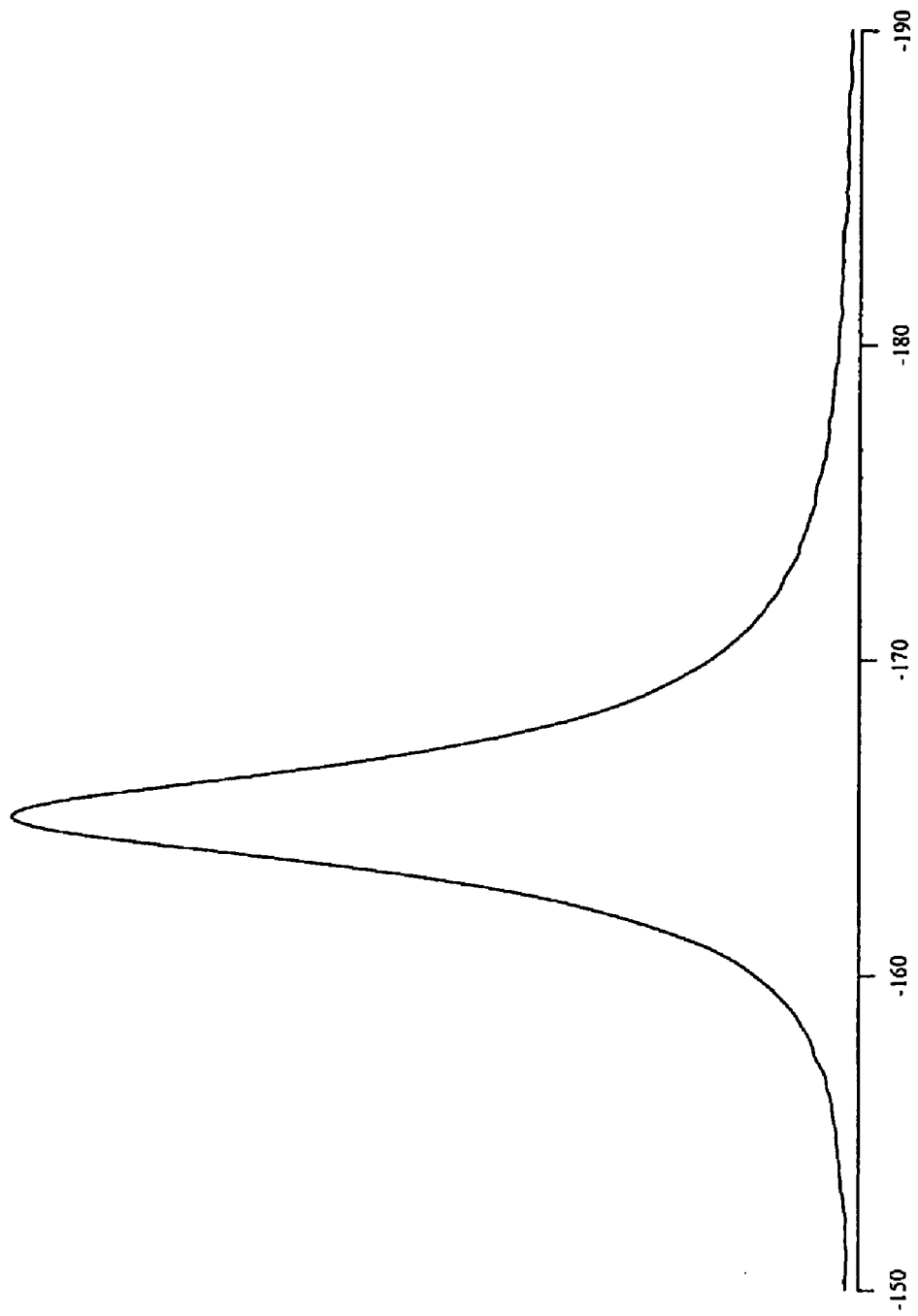
FIG. 7 is a fluorine-19 magic-angle spinning (MAS) nuclear magnetic resonance (NMR) spectrum of the crystalline monohydrate form of Compound I of the present invention.

FIG. 7 shows the solid-state fluorine-19 MAS NMR spectrum for the crystalline monohydrate form of Compound I. The crystalline monohydrate exhibited an isotropic peak at −165 p.p.m.

Figure 8:
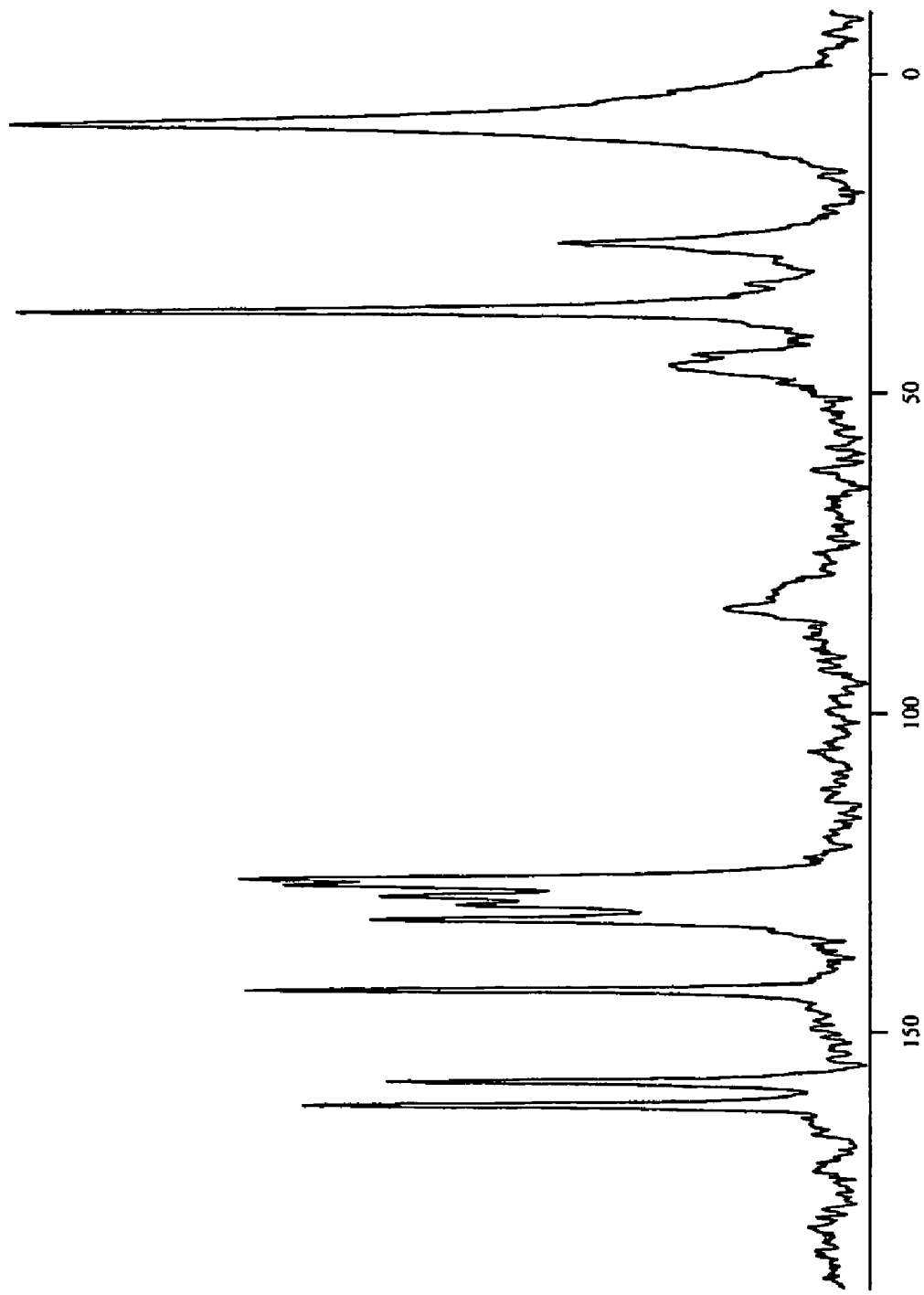
FIG. 8 is a carbon-13 cross-polarization magic-angle spinning (CPMAS) nuclear magnetic resonance (NMR) spectrum of the crystalline monohydrate form of Compound I of the present invention.

FIG. 8 shows the solid state carbon-13 CPMAS NMR spectrum for the crystalline monohydrate form of Compound I. The crystalline monohydrate form exhibited characteristic signals with chemical shift values of 161.5, 157.8, 143.4, 132.3, 130.0, 128.5, 126.9, 125.9, 45.5, 37.2, 26.4, and 7.7 p.p.m.

Figure 12:
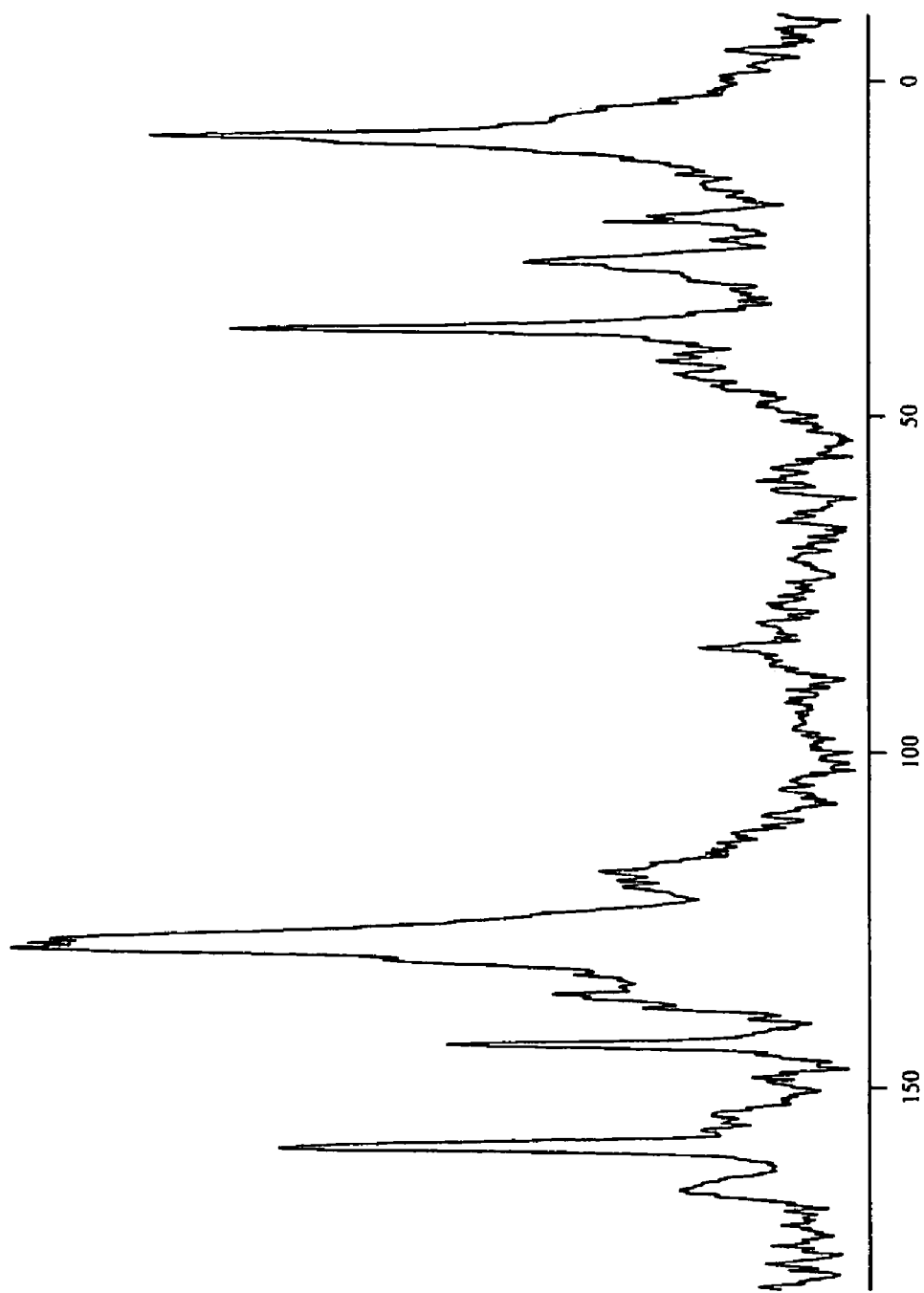
FIG. 12 is a carbon-13 cross-polarization magic-angle spinning (CPMAS) nuclear magnetic resonance (NMR) spectrum of the crystalline toluene solvate of Compound I of the present invention.

FIG. 12 shows the solid state carbon-13 CPMAS NMR spectrum for the crystalline toluene solvate of Compound I. The crystalline toluene solvate exhibited characteristic signals with chemical shift values of 165.2, 158.8, 143.5, 136.0, 128.8, 128.0, 127.4, 120.0, 119.0, 117.6, 36.6, 26.8, 21.0, and 7.8 p.p.m.

DSC data were acquired using TA Instruments DSC 2910 or equivalent instrumentation was used. Between 2 and 6 mg sample was weighed into an open pan. This pan was then crimped and placed at the sample position in the calorimeter cell. An empty pan was placed at the reference position. The calorimeter cell was closed and a flow of nitrogen was passed through the cell. The heating program was set to heat the sample at a heating rate of 10° C./min to a temperature of approximately 250° C. The heating program was started. When the run was completed, the data were analyzed using the DSC analysis program contained in the system software. The melting endotherm was integrated between baseline temperature points that are above and below the temperature range over which the endotherm was observed. The data reported are the onset temperature, peak temperature and enthalpy.

Figure 4:
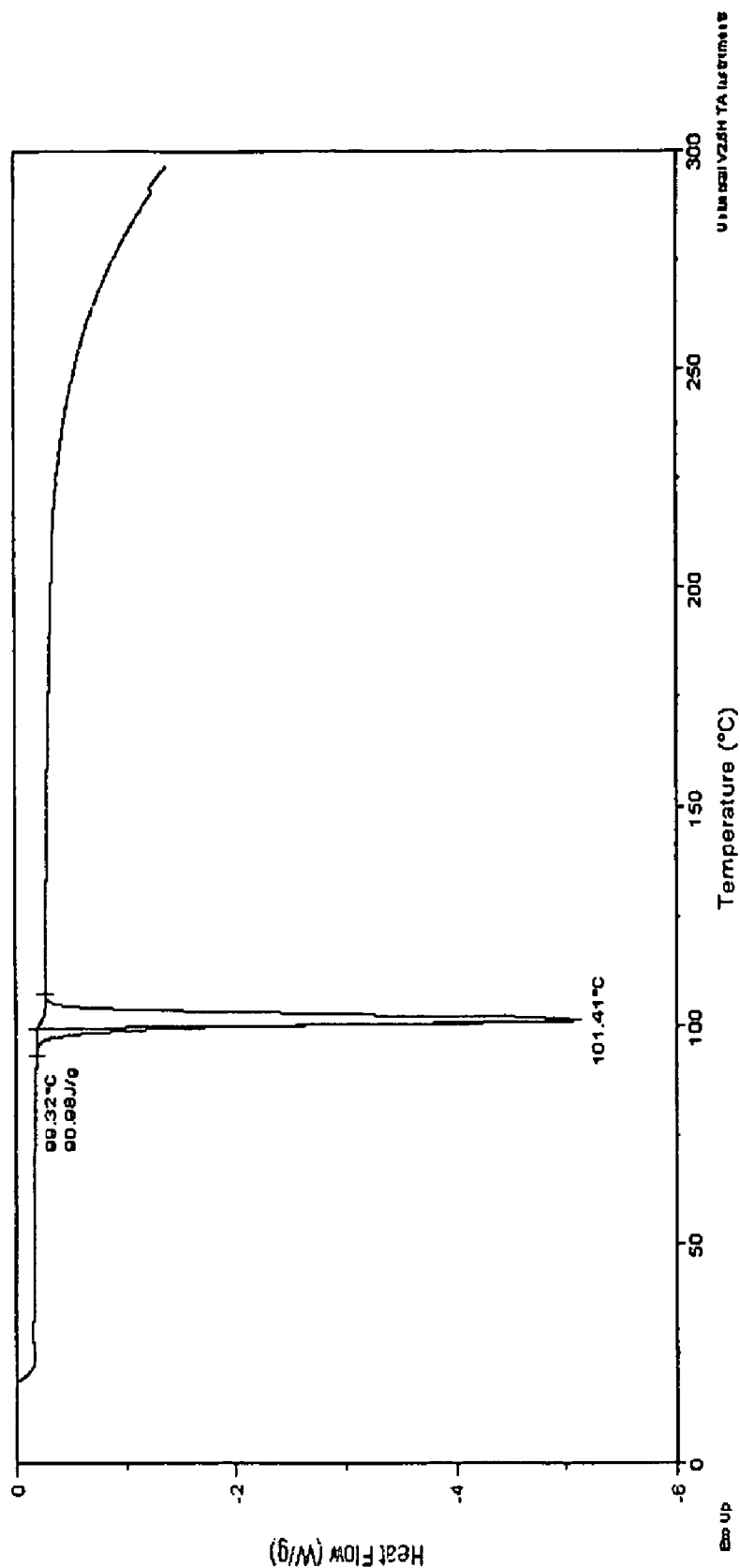
FIG. 4 is a typical differential scanning calorimetry (DSC) curve of the crystalline anhydrate form of Compound I of the present invention.

FIG. 4 shows the differential calorimetry scan for the crystalline anhydrate form of Compound I. The crystalline anhydrate form exhibited a melting endotherm with an onset temperature of 99.3° C., a peak temperature of 101.4° C., and an enthalpy of 91.0 J/g.

Figure 9:
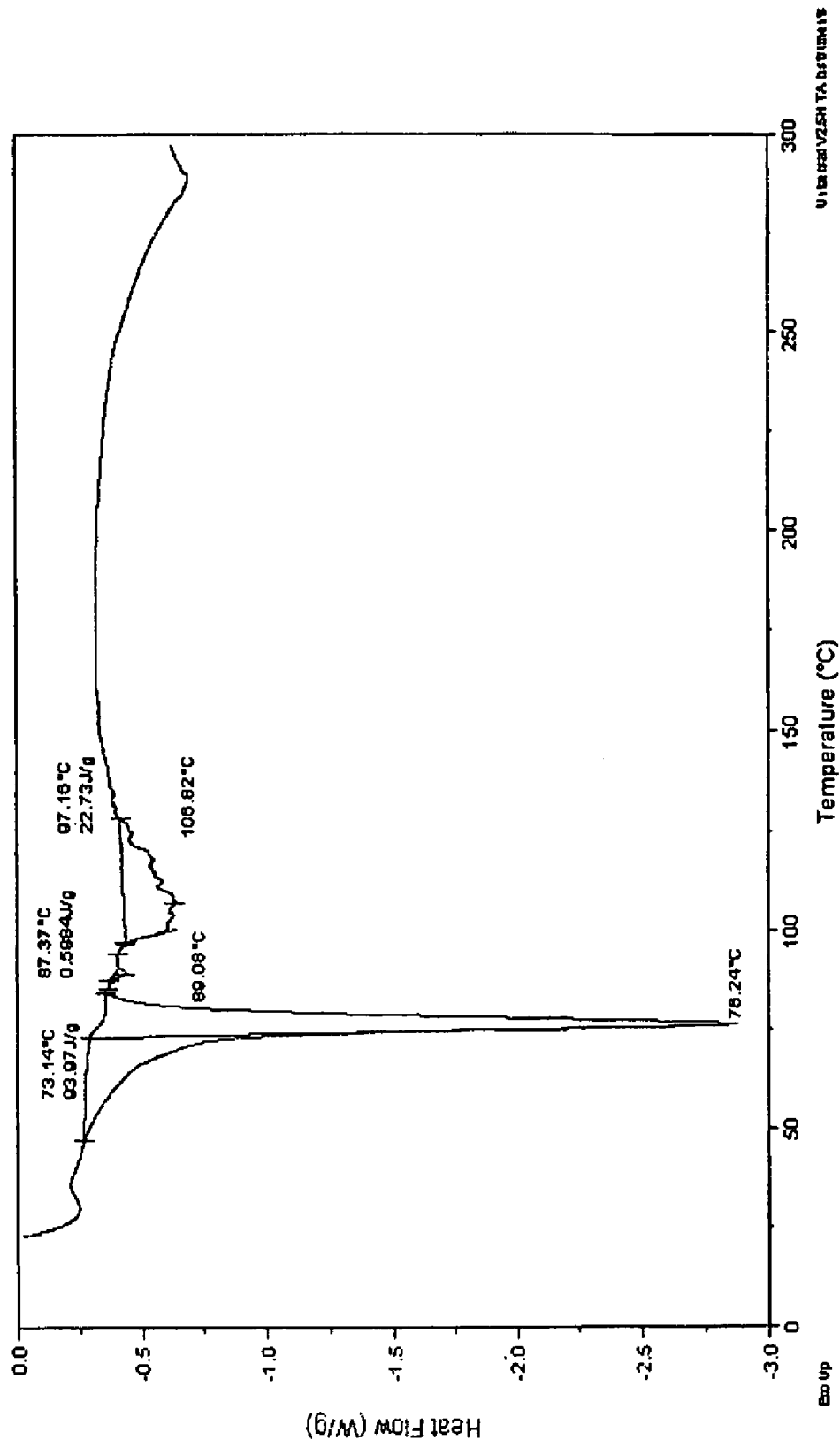
FIG. 9 is a typical DSC curve of the crystalline monohydrate form of Compound I of the present invention.

FIG. 9 shows the differential calorimetry scan for crystalline monohydrate form of Compound I. The crystalline monohydrate form exhibited a first endotherm with an onset temperature of 73.1° C., a peak temperature of 76.2° C., and an enthalpy of 94.0 J/g.

Figure 13:
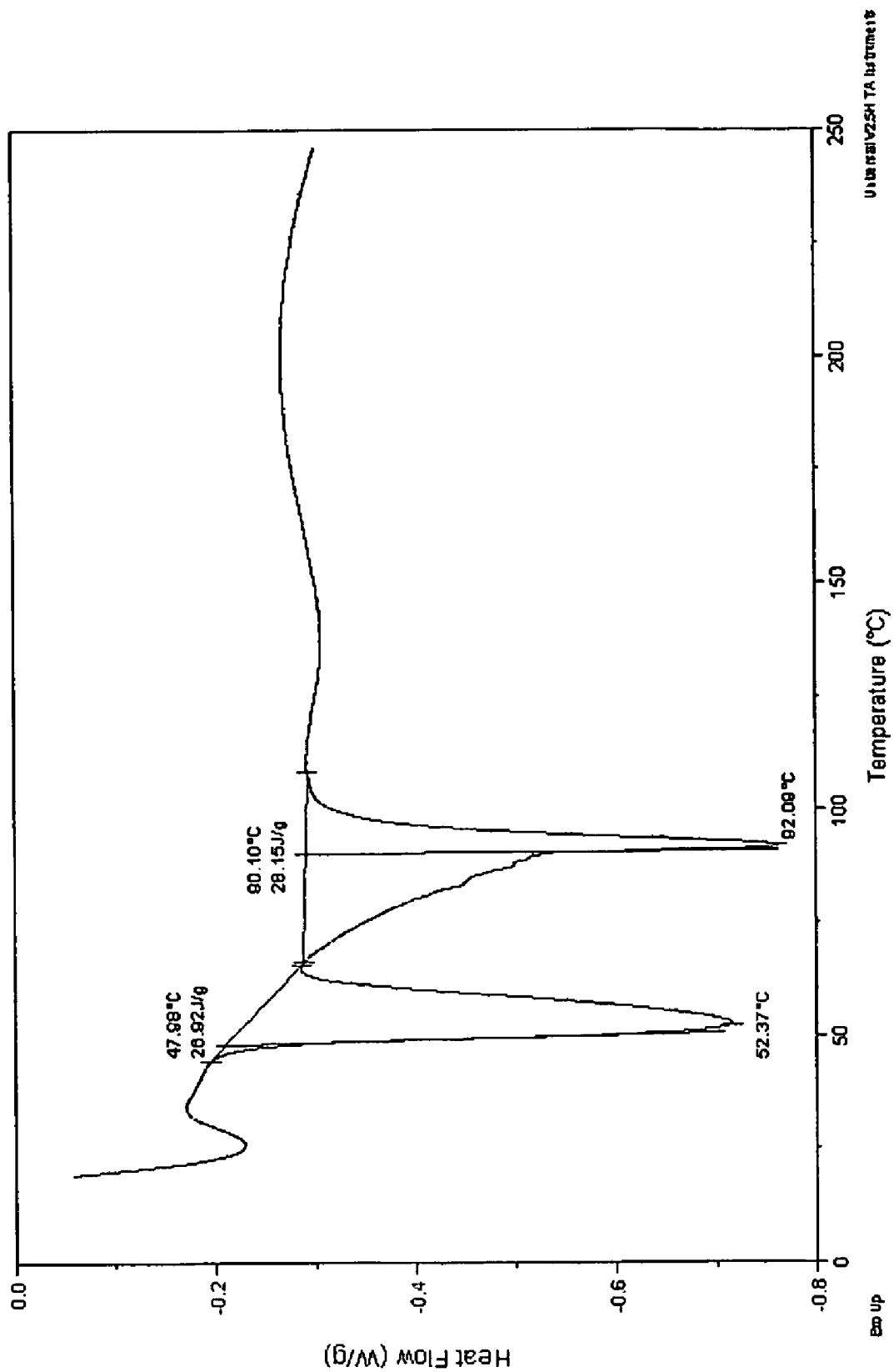
FIG. 13 is a typical differential scanning calorimetry (DSC) curve of the crystalline toluene solvate of Compound I of the present invention.

FIG. 13 shows the differential calorimetry scan for the crystalline toluene solvate of Compound I. The crystalline toluene solvate exhibited a melting endotherm with an onset temperature of 48.0° C., a peak temperature of 52.4° C., and an enthalpy of 26.9 J/g. The first thermal event was followed by a second endotherm, with an onset temperature of 90.1° C. and a peak temperature of 92.1° C.

A Perkin Elmer model TGA 7 or equivalent instrument was used to obtain the TGA curves. Experiments were performed under a flow of nitrogen and using a heating rate of 10° C./min to a maximum temperature of approximately 250° C. After automatically taring the balance, 5 to 20 mg of sample was added to the platinum pan, the furnace was raised, and the heating program started. Weight/temperature data were collected automatically by the instrument. Analysis of the results was carried out by selecting the Delta Y function within the instrument software and choosing the temperatures between which the weight loss was to be calculated. Weight losses are reported up to the onset of decomposition/evaporation.

Figure 5:
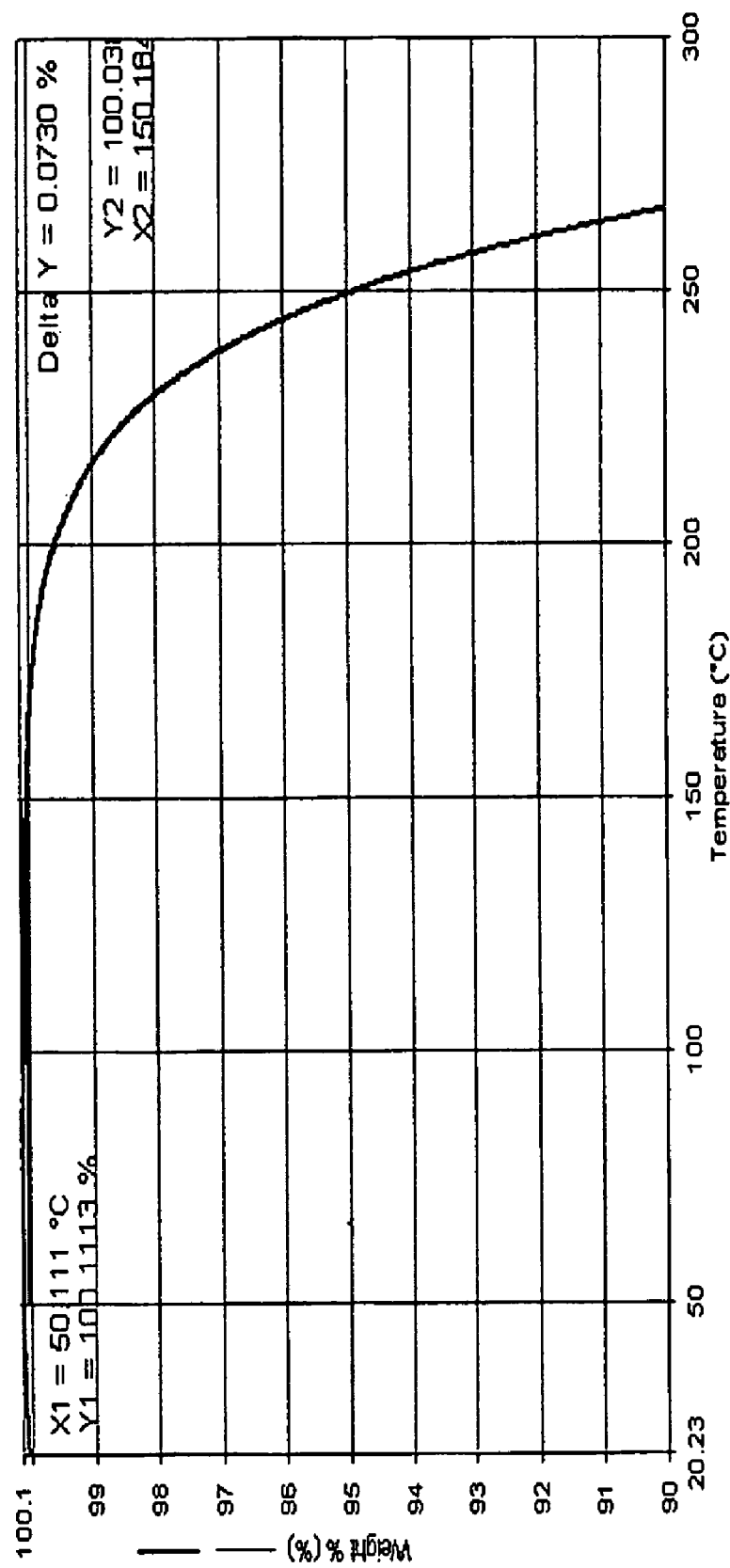
FIG. 5 is a typical thermogravimetric analysis (TGA) curve of the crystalline anhydrate form of Compound I of the present invention.

FIG. 5 shows a characteristic thermogravimetric analysis (TGA) curve for the crystalline anhydrate form of Compound I. TGA indicated a weight loss of about 0.1% from about 50° C. to about 150° C.

Figure 10:
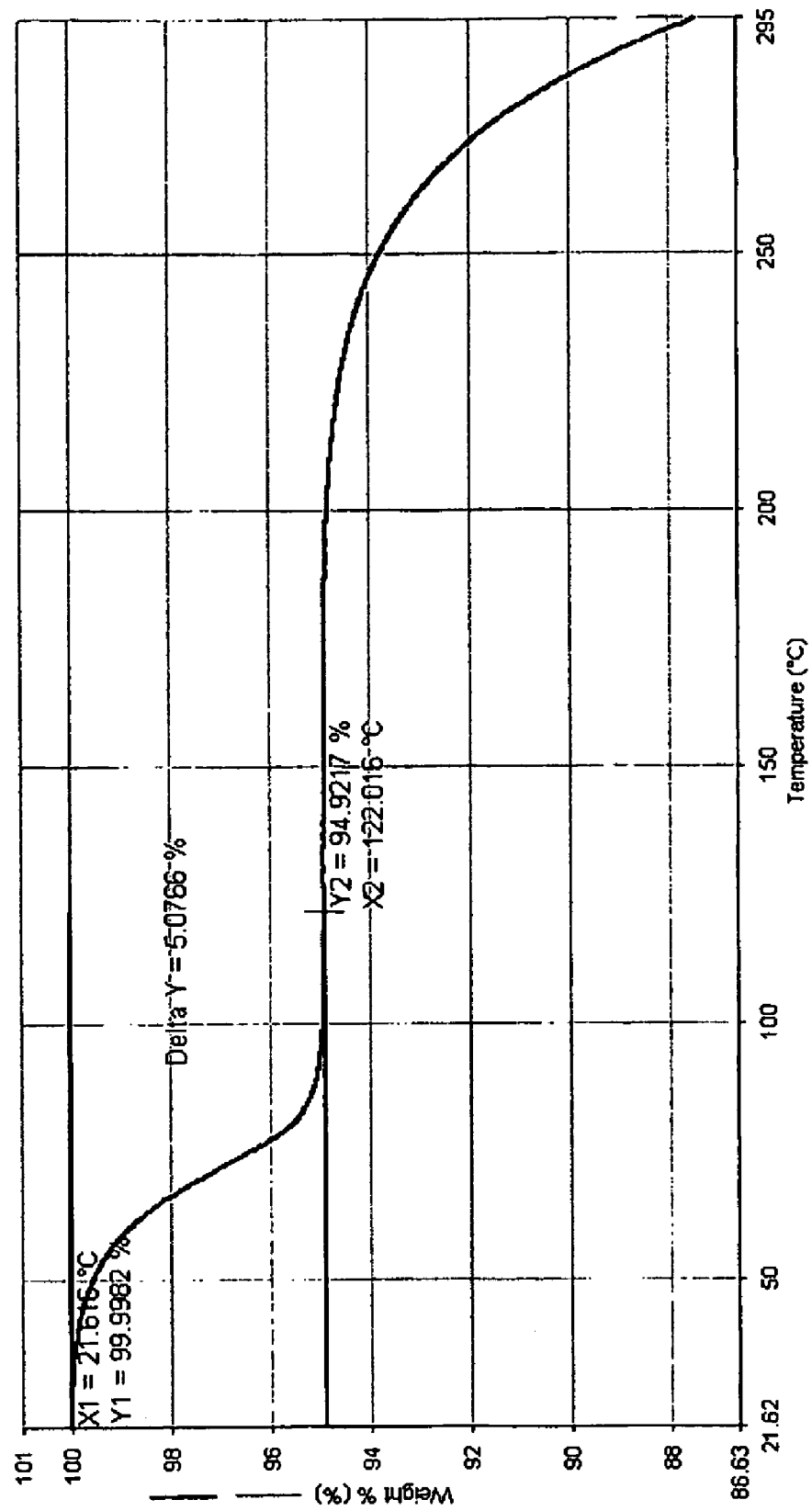
FIG. 10 is a typical TGA curve of the crystalline monohydrate form of Compound I of the present invention.

FIG. 10 shows a characteristic thermogravimetric analysis (TGA) curve for the crystalline monohydrate form of Compound I. TGA indicated a weight loss of about 5.1% from about 22° C. to about 122° C. This weight loss is consistent with the amount of water present in the monohydrate form.

Figure 14:
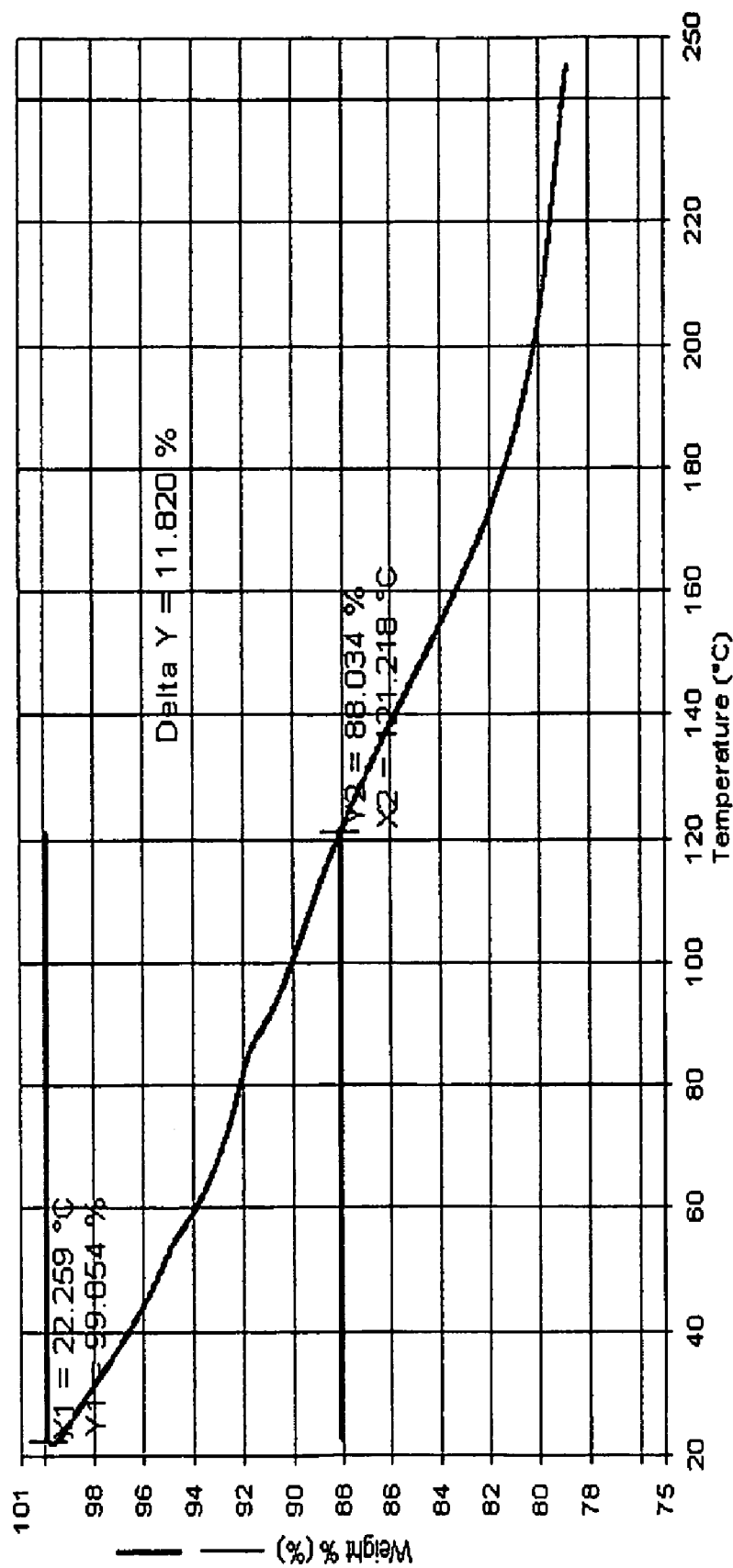
FIG. 14 is a typical thermogravimetric analysis (TGA) curve of the crystalline toluene solvate of Compound I of the present invention.

FIG. 14 shows a characteristic thermogravimetric analysis (TGA) curve for the crystalline toluene solvate of Compound I. TGA indicated a weight loss of about 10% from about 22° C. to about 121° C. This weight loss is consistent with a toluene hemi-solvate form.

The crystalline Compound I anhydrate or monohydrate form of the present invention has a phase purity of at least about 5% of anhydrate or monohydrate with the above X-ray powder diffraction, fluorine-19 MAS NMR, carbon-13 CPMAS NMR, and DSC physical characteristics. In one embodiment the phase purity is at least about 10% of anhydrate or monohydrate with the above solid-state physical characteristics. In a second embodiment the phase purity is at least about 25% of anhydrate or monohydrate with the above solid-state physical characteristics. In a third embodiment the phase purity is at least about 50% of anhydrate or monohydrate with the above solid-state physical characteristics. In a fourth embodiment the phase purity is at least about 75% of anhydrate or monohydrate with the above solid-state physical characteristics. In a fifth embodiment the phase purity is at least about 90% of anhydrate or monohydrate with the above solid-state physical characteristics. In a sixth embodiment the crystalline Compound I is the substantially phase pure anhydrate or monohydrate with the above solid-state physical characteristics. By the term "phase purity" is meant the solid state purity of the Compound I anhydrate or monohydrate form with regard to another particular crystalline polymorph or amorphous form of Compound I as determined by the solid-state physical methods described in the present application.

Example of A Pharmaceutical Composition

The crystalline anhydrate form was formulated into a capsule formulation as follows. A 100 mg potency capsule was composed of 100 mg of the API, 190 mg of microcrystalline cellulose; and about 95 mg gelatin as in #0 white opaque gelatin capsule. The API and microcrystalline cellulose were first blended, and the mixture was then encapsulated in gelatin capsules.

What is claimed is:

1. Crystalline 3-[1-(4-Chlorophenyl)-trans-3-fluorocyclobutyl]-4,5-dicyclopropyl-r-4H-1,2,4-triazole anhydrate of structural formula I:

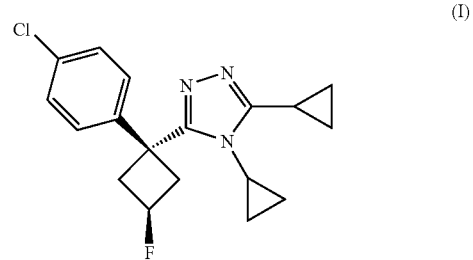

characterized by characteristic reflections obtained from the X-ray powder diffraction pattern at spectral d-spacings of 7.19, 6.09, 4.57, 4.19, 4.06, and 3.20 angstroms.

2. The crystalline anhydrate of claim 1 further characterized by the X-ray powder diffraction pattern of FIG. 1.

3. Crystalline 3-[1-(4-Chlorophenyl)-trans-3-fluorocyclobutyl]-4,5-dicyclopropyl-r-4H-1,2,4-triazole anhydrate of structural formula I:

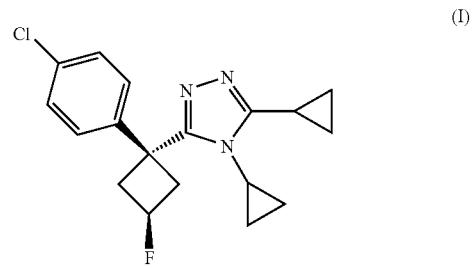

characterized by the solid state fluorine-19 MAS nuclear magnetic resonance spectrum of FIG. 2.

4. Crystalline 3-[1-(4-Chlorophenyl)-trans-3-fluorocyclobutyl]-4,5-dicyclopropyl-r-4H-1,2,4-triazole anhydrate of structural formula I:

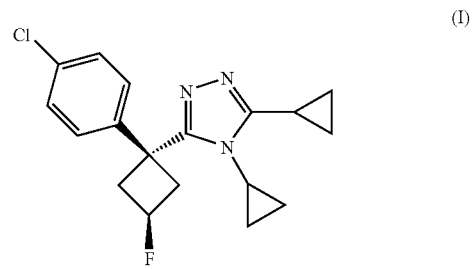

characterized by a solid-state carbon-13 CPMAS nuclear magnetic resonance spectrum showing signals with chemical shift values of 158.9, 158.2, 143.0, 129.3, 127.2, 43.5, 36.6, 26.4, and 7.6 p.p.m.

5. The crystalline anhydrate of claim 4 characterized by the solid-state carbon-13 CPMAS nuclear magnetic resonance spectrum of FIG. 3.

6. Crystalline 3-[1-(4-Chlorophenyl)-trans-3-fluorocyclobutyl]-4,5-dicyclopropyl-r-4H-1,2,4-triazole anhydrate of structural formula I:

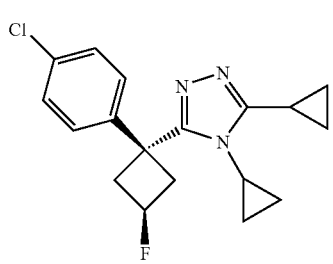

(I)

characterized by the differential scanning calorimetric (DSC) curve of FIG. 4.

7. Crystalline 3-[1-(4-Chlorophenyl)-trans-3-fluorocyclobutyl]-4,5-dicyclopropyl-r-4H-1,2,4-triazole anhydrate of structural formula I:

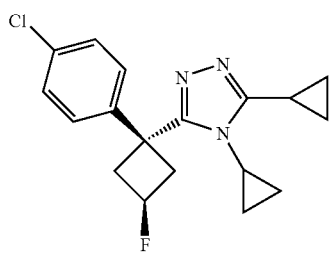

(I)

characterized by the thermogravimetric analyis (TGA) curve of FIG. 5.

8. Crystalline 3-[1-(4-Chlorophenyl)-trans-3-fluorocyclobutyl]-4,5-dicyclopropyl-r-4H-1,2,4-triazole monohydrate of structural formula I:

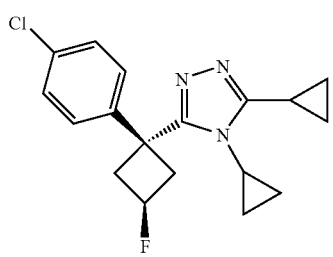

(I)

characterized by characteristic reflections obtained from the X-ray powder diffraction pattern at spectral d-spacings of 8.08, 6.49, 5.43, 5.39, 4.38, 4.10, 3.18, and 2.74 angstroms.

9. The crystalline monohydrate of claim 8 further characterized by the X-ray powder diffraction pattern of FIG. 6.

10. Crystalline 3-[1-(4-Chlorophenyl)-trans-3-fluorocyclobutyl]-4,5-dicyclopropyl-r-4H-1,2,4-triazole monohydrate of structural formula I:

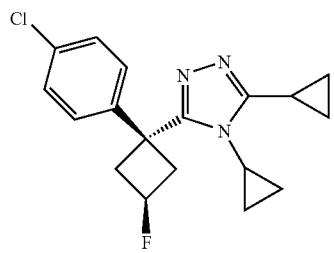

(I)

characterized by the solid state fluorine-19 MAS nuclear magnetic resonance spectrum of FIG. 7.

11. Crystalline 3-[1-(4-Chlorophenyl)-trans-3-fluorocyclobutyl]-4,5-dicyclopropyl-r-4H-1,2,4-triazole monohydrate of structural formula I:

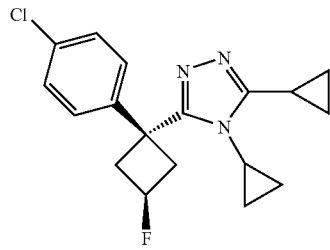

(I)

characterized by a solid-state carbon-13 CPMAS nuclear magnetic resonance spectrum showing signals with chemical shift values of 161.5, 157.8, 143.4, 132.3, 130.0, 128.5, 126.9, 125.9, 45.5, 37.2, 26.4, and 7.7 p.p.m.

12. The crystalline monohydrate of claim 11 characterized by the solid-state carbon-13 CPMAS nuclear magnetic resonance spectrum of FIG. 8.

13. Crystalline 3-[1-(4-Chlorophenyl)-trans-3-fluorocyclobutyl]-4,5-dicyclopropyl-r-4H-1,2,4-triazole monohydrate of structural formula I:

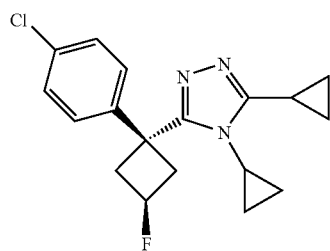

(I)

characterized by the differential scanning calorimetric (DSC) curve of FIG. 9.

14. Crystalline 3-[1-(4-Chlorophenyl)-trans-3-fluorocyclobutyl]-4,5-dicyclopropyl-r-4H-1,2,4-triazole monohydrate of structural formula I:

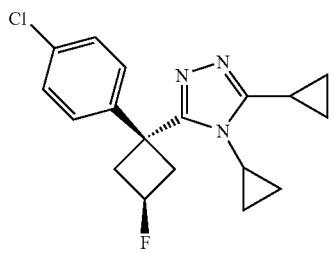

characterized by the thermogravimetric analyis (TGA) curve of FIG. 10.

15. Crystalline 3-[1-(4-Chlorophenyl)-trans-3-fluorocyclobutyl]-4,5-dicyclopropyl-r-4H-1,2,4-triazole toluene solvate of structural formula I:

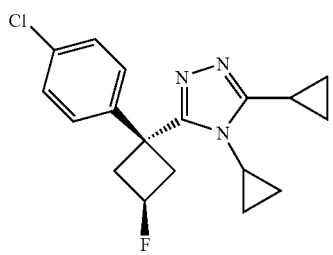

characterized by characteristic reflections obtained from the X-ray powder diffraction pattern at spectral d-spacings of 7.13, 6.74, 5.95, 4.38, 3.83, 3.61, 3.42, 3.14, and 2.30 angstroms.

16. The crystalline toluene solvate of claim 15 further characterized by the X-ray powder diffraction pattern of FIG. 11.

17. Crystalline 3-[1-(4-Chlorophenyl)-trans-3-fluorocyclobutyl]-4,5-dicyclopropyl-r-4H-1,2,4-triazole toluene solvate of structural formula I:

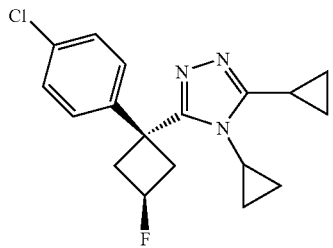

characterized by a solid-state carbon-13 CPMAS nuclear magnetic resonance spectrum showing signals with chemical shift values of 165.2, 158.8, 143.5, 136.0, 128.8, 128.0, 127.4, 120.0, 119.0, 117.6, 36.6, 26.8, 21.0, and 7.8 p.p.m.

18. The crystalline toluene solvate of claim 17 characterized by the solid-state carbon-13 CPMAS nuclear magnetic resonance spectrum of FIG. 12.

19. Crystalline 3-[1-(4-Chlorophenyl)-trans-3-fluorocyclobutyl]-4,5-dicyclopropyl-r-4H-1,2,4-triazole toluene solvate of structural formula I:

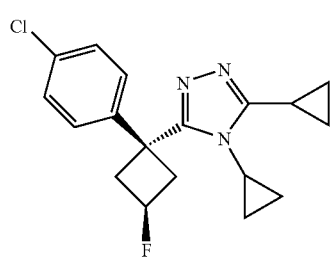

characterized by the differential scanning calorimetric (DSC) curve of FIG. 13.

20. Crystalline 3-[1-(4-Chlorophenyl)-trans-3-fluorocyclobutyl]-4,5-dicyclopropyl-r-4H-1,2,4-triazole of toluene solvate structural formula I:

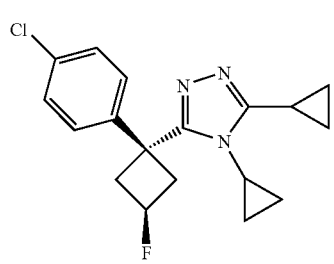

characterized by the thermogravimetric analysis (TGA) curve of FIG. 14.

* * * * *